United States Patent [19]

Lee et al.

[11] Patent Number: 5,919,437
[45] Date of Patent: *Jul. 6, 1999

[54] COSMETIC CREAM COMPOSITION CONTAINING SILICONE GEL MATERIAL

[75] Inventors: Wilson Lee, Bloomfield; Robert J. Bianchini, Belle Mead; Peter R. Hilliard, Jr., Far Hills, all of N.J.

[73] Assignee: Colgate-Palmolive Company, New York, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/653,363

[22] Filed: May 24, 1996

[51] Int. Cl.⁶ .......................... A61K 7/38; A61K 31/74; C08G 77/06; C08G 77/04
[52] U.S. Cl. .................... 424/68; 514/944; 424/78.03; 528/15; 528/34
[58] Field of Search .................. 424/68, 78.03; 514/944; 528/15, 34

[56] References Cited

U.S. PATENT DOCUMENTS

| | | | |
|---|---|---|---|
| 4,083,956 | 4/1978 | Shelton | 424/66 |
| 4,268,499 | 5/1981 | Keil | 424/68 |
| 4,311,695 | 1/1982 | Starch | 424/184 |
| 4,322,400 | 3/1982 | Yuhas | 424/59 |
| 4,350,605 | 9/1982 | Hughett | 252/305 |
| 4,355,020 | 10/1982 | Kuy | 424/28 |
| 4,423,041 | 12/1983 | Clum et al. | 424/184 |
| 4,435,382 | 3/1984 | Shin et al. | 424/66 |
| 4,499,069 | 2/1985 | Krafton | 424/66 |
| 4,526,780 | 7/1985 | Marschner et al. | 424/66 |
| 4,673,570 | 6/1987 | Soldati | 424/66 |
| 4,698,386 | 10/1987 | Fujimoto | 524/862 |
| 4,749,569 | 6/1988 | Gianino et al. | 424/65 |
| 4,774,079 | 9/1988 | Shin et al. | 424/66 |
| 4,782,095 | 11/1988 | Gum | 514/937 |
| 4,784,844 | 11/1988 | Thimineur et al. | 424/65 |
| 4,797,272 | 1/1989 | Linn et al. | 424/59 |
| 4,797,273 | 1/1989 | Linn et al. | 424/59 |
| 4,801,447 | 1/1989 | Gum | 424/68 |
| 4,853,214 | 8/1989 | Orr | 424/69 |
| 4,871,525 | 10/1989 | Giovanniello et al. | 423/463 |
| 4,902,499 | 2/1990 | Bolish, Jr. et al. | 424/70 |
| 4,937,069 | 6/1990 | Shin | 424/66 |
| 4,980,156 | 12/1990 | Raleigh et al. | 424/66 |
| 4,988,504 | 1/1991 | Zotto et al. | 424/65 |
| 5,000,356 | 3/1991 | Johnson et al. | 222/391 |
| 5,002,762 | 3/1991 | Bolich | 424/70 |
| 5,019,375 | 5/1991 | Tanner et al. | 424/66 |
| 5,069,897 | 12/1991 | Orr | 424/66 |
| 5,086,147 | 2/1992 | Ikeno | 528/15 |
| 5,102,656 | 4/1992 | Kasat | 424/66 |
| 5,135,742 | 8/1992 | Halloran et al. | 424/70 |
| 5,147,965 | 9/1992 | Ichinohe et al. | 528/12 |
| 5,156,834 | 10/1992 | Beckmeyer et al. | 424/47 |
| 5,160,732 | 11/1992 | Katsoulis et al. | 424/68 |
| 5,169,626 | 12/1992 | Tanner et al. | 424/66 |
| 5,185,144 | 2/1993 | Koslo et al. | 424/66 |
| 5,202,115 | 4/1993 | Viacenti et al. | 424/66 |
| 5,202,123 | 4/1993 | Katsoulis et al. | 424/401 |
| 5,211,941 | 5/1993 | Komori et al. | 424/70 |
| 5,216,033 | 6/1993 | Pereira et al. | 514/844 |
| 5,225,188 | 7/1993 | Abrutyn et al. | 424/66 |
| 5,236,986 | 8/1993 | Sakuta | 524/267 |
| 5,266,321 | 11/1993 | Shukuzaki et al. | 424/401 |
| 5,279,890 | 1/1994 | Ikeno et al. | 428/217 |
| 5,302,381 | 4/1994 | Greczyn et al. | 424/66 |
| 5,310,842 | 5/1994 | Ichinohe et al. | 528/12 |
| 5,384,117 | 1/1995 | Vu et al. | 424/66 |
| 5,412,004 | 5/1995 | Tachibana et al. | 524/27 |
| 5,466,442 | 11/1995 | Ohashi et al. | 424/70.12 |
| 5,466,849 | 11/1995 | Shioya et al. | 556/445 |
| 5,552,476 | 9/1996 | Halling | 524/837 |
| 5,565,194 | 10/1996 | Burkhort et al. | 424/70.12 |
| 5,587,153 | 12/1996 | Angelong, Jr. et al. | 424/66 |
| 5,589,196 | 12/1996 | Callaghan et al. | 424/617 |
| 5,593,663 | 1/1997 | Leng et al. | 424/65 |

(List continued on next page.)

FOREIGN PATENT DOCUMENTS

| | | |
|---|---|---|
| 0135315 | 3/1985 | European Pat. Off. . |
| 0 197 485 A2 | 4/1986 | European Pat. Off. . |
| 0 284 765 A2 | 2/1988 | European Pat. Off. . |
| 0322118 | 6/1989 | European Pat. Off. . |
| 0410697 | 7/1990 | European Pat. Off. . |
| 0383540 | 8/1990 | European Pat. Off. . |
| 0 431 979 A2 | 12/1990 | European Pat. Off. . |
| 0431979 | 12/1990 | European Pat. Off. . |
| 0444960 | 3/1991 | European Pat. Off. . |
| 0475439 | 9/1991 | European Pat. Off. . |
| 0 501 791 A2 | 2/1992 | European Pat. Off. . |
| 0501791 | 2/1992 | European Pat. Off. . |
| 0501791 | 9/1992 | European Pat. Off. . |
| 0614658 | 3/1994 | European Pat. Off. . |
| 0688828 | 2/1995 | European Pat. Off. . |
| 0787758 | 2/1995 | European Pat. Off. . |
| 0676193 | 10/1995 | European Pat. Off. . |
| 62-143970 | 12/1985 | Japan . |
| 62-143971 | 12/1985 | Japan . |
| 6-173618 | 11/1994 | Japan . |
| WO06594 | 3/1996 | WIPO . |
| WO 97/12584 | 4/1997 | WIPO . |
| WO04236 | 2/1998 | WIPO . |

*Primary Examiner*—Frank C. Eisenschenk
*Assistant Examiner*—Hankyel T. Park
*Attorney, Agent, or Firm*—William I. Solomon; Richard J. Ancel; Rosemary M. Miano

[57] ABSTRACT

Disclosed is a solid cosmetic composition (e.g., a cream composition) containing an active cosmetic material (e.g., a deodorant active, an antiperspirant active, a sunscreen, an insect repellent and/or an anti-fungal agent) and a silicone gel material. The silicone gel material includes (a) a volatile silicone material and (b) an organopolysiloxane material as a gelling agent, able to form a gel after being mixed with the volatile silicone material. The organopolysiloxane material can be a reaction product of a vinyl-terminated siloxane polymer and a hydride cross-linking agent. The composition can be formed by mixing the active cosmetic material and silicone gel material at ambient temperature. The compositions do not need particulate or clay thickeners or waxy gelling agents.

46 Claims, No Drawings

U.S. PATENT DOCUMENTS

| | | | |
|---|---|---|---|
| 5,595,729 | 1/1997 | Barr et al. | 424/68 |
| 5,599,533 | 2/1997 | Stepniewski et al. | 424/78.02 |
| 5,623,017 | 4/1997 | Hill | 524/860 |
| 5,626,827 | 5/1997 | Barr et al. | 423/412 |
| 5,626,857 | 5/1997 | Thimineur e t al. | 424/401 |
| 5,637,401 | 6/1997 | Berman et al. | 252/315.2 |
| 5,643,555 | 7/1997 | Collin et al. | 424/59 |
| 5,645,842 | 7/1997 | Grüning et al. | 424/401 |
| 5,650,146 | 7/1997 | Shaw | 424/78.03 |
| 5,665,804 | 9/1997 | Hill et al. | 524/268 |

COSMETIC CREAM COMPOSITION CONTAINING SILICONE GEL MATERIAL

BACKGROUND OF THE INVENTION

The present invention is directed to a solid cosmetic composition which leaves substantially no visible (white) residue on the skin, which has good cosmetic properties (e.g., a silky and non-greasy feel), and which exhibits reduced syneresis. In particular, the present invention is directed to a solid (for example, a cream) cosmetic composition containing at least one active cosmetic material (e.g., selected from deodorant active materials, antiperspirant active materials, sunscreen materials, insect repellents and anti-fungal agents), which leaves substantially no visible residue on the skin and which has the aforementioned good cosmetic properties and reduced syneresis.

The present invention especially relates to an antiperspirant cream composition containing an antiperspirant active agent (for example, an antiperspirant active metal salt, such as an antiperspirant active aluminum salt), and to a deodorant cream composition containing a deodorant active agent (for example, a bacteriostat, such as Triclosan), which exhibit the aforementioned properties.

Antiperspirant products are well known in the art. Antiperspirant products have appeared in the market in various dosage forms, such as sticks, gels, roll-ons, aerosols and creams. Of these dosage forms, e.g., various sticks, gels and creams are constituted by a liquid base material solidified by a solidifying agent, and these fall within solid cosmetic compositions according to the present invention. Generally, the dosage forms include a solution of the active ingredient in a suitable solvent, a suspension of the active ingredient in a non-solvent, or a multiphasic dispersion or emulsion in which a solution of the active ingredient is dispersed in some continuous phase or in which the solubilized active ingredient constitutes the continuous phase.

A variety of cream formulations (also known as soft solids or semi-solids) are known. Various of these cream formulations include a clay thickening agent, and an activator for such clay thickening agent. See, for example, U.S. Pat. No. 5,019,375 to Tanner, et al.; and U.S. Pat. No. 4,526,780 to Marschner, et al.

Other cream compositions contain a particulate thickening agent such as fumed silica. See U.S. Pat. No. 5,069,897 to Orr and U.S. Pat. No. 4,937,069 to Shin.

U.S. Pat. No. 5,225,188 to Abrutyn, et al. discloses underarm formulations, containing specific volatile and/or non-volatile alkylmethylsiloxanes, having desirable characteristics such as modified hardness, reduced whitening, improved feel, compatibilization of ingredients, and controlled vapor pressure. This patent discloses that the described underarm formulations can include, for example, antiperspirant and/or deodorant formulations and the like. This patent further discloses that conventional underarm formulations, especially sticks, contained waxy materials to provide a structure which can be sheared when applied to the skin; and that some or all of these waxes may be replaced with the specified alkylmethylsiloxanes, although the formulatioms described therein can also include conventional waxes. The disclosed formulations containing the specified alkylmethylsiloxanes were manufactured at high temperatures (e.g., temperatures of 70° C.).

U.S. Pat. No. 5,102,656 to Kasat, the contents of which are incorporated herein by reference in their entirety, discloses a creamy, heterogeneous, anhydrous antiperspirant product containing, in percent by weight of the total weight of the composition, 30–70% of a volatile silicone product as a carrier, 7–30% of a suitable gelling agent or agents, and about 12–30% of a physiologically acceptable antiperspirant agent. This patent discloses that the gelling agent can be any of a number of compositions, including, for example, hydrogenated vegetable oil, hydrogenated castor oil, fatty acids, beeswax, paraffin wax, fatty alcohols, polyethylene and the like. This patent discloses that the compositions are formed by heating all ingredients except the fragrance, if any, to a temperature above the melting point of the gelling agent; cooling (while mixing is continued) and then adding the fragrance, if any, while continuing to mix, and then cooling further (while still mixing), the product then being charged into dispensers and allowed to come to room temperature.

Notwithstanding all of the foregoing, it is still desired to provide a cosmetic composition that is stable, substantially anhydrous, and free of conventional gelling agents such as fatty alcohols and hydrogenated castor oil, and which is free of syneresis and has good cosmetic properties (including substantially no visible residue upon application and after drying, and a silky and non-greasy feel). It is also desired to provide such cosmetic composition which is easy to manufacture, and which can be manufactured at room temperature. It is particularly desired to provide an antiperspirant and/or deodorant composition having the aforementioned cosmetic properties and which is easy to manufacture with room temperature processing.

SUMMARY OF THE INVENTION

Accordingly, it is a first object of the present invention to provide a cosmetic composition (e.g., a solid cosmetic composition) which leaves substantially no visible (white) residue on the skin, and which has good cosmetic properties (e.g., a silky and non-greasy feel), and a method of making and a method of using the same.

It is a further object of the present invention to provide a cosmetic composition having reduced syneresis (e.g., reduced syneresis of silicone material therefrom), and methods of making and using such composition.

It is a further object of the present invention to provide a cosmetic composition that is easy to manufacture, and which can be made/processed at ambient temperatures.

It is a still further object of the present invention to provide a cosmetic composition, in the form of a solid (as defined previously herein), which contains no conventional waxy materials and which is substantially anhydrous.

It is a still further object of the present invention to provide a cosmetic composition which has long-lasting fragrance substantivity, and methods of making and of using such composition.

It is a still further object of the present invention to provide an antiperspirant or deodorant composition for reducing body malodor, having the aforementioned good cosmetic properties and which leaves substantially no visible residue on the skin, and methods of making and using such composition.

It is a still further object of the present invention to provide an antiperspirant composition for reducing perspiration from axillary regions of the human body, the composition containing antiperspirant active materials in particulate form in a carrier, the composition having good cosmetic properties and which leaves substantially no visible residue on the skin.

It is a still further object of the present invention to provide a cosmetic cream composition (e.g., an antiperspirant cream or deodorant cream), having the aforementioned good cosmetic properties and reduced syneresis, which leaves substantially no visible residue on the skin and which is easy manufacture, with room temperature (ambient) processing.

The foregoing objects are achieved by the cosmetic composition of the present invention, containing (1) an active cosmetic material and (2) a silicone gel material, the silicone gel material including an organopolysiloxane material as a gelling (solidifying) agent and a volatile silicone material as a solvent for the gelling agent (that is, the volatile silicone material is a liquid base material of the composition). The active cosmetic material can be selected from deodorant materials, antiperspirant materials, sunscreen agents, insect repellents and anti-fungal agents, and is included in the composition in an amount so as to have a functional effect (e.g., provides its intended function to reduce malodor, reduce perspiration, screen the sun's rays, etc.). The organopolysiloxane material is included in the composition in an amount sufficient to provide a solid (solidified) cosmetic composition, while the volatile silicone material is included in the composition in an amount such that the organopolysiloxane material can be gelled therefrom (for example, the organopolysiloxane material can be swelled by the volatile silicone material, so as to form the gel).

The product "REVELATION" by "ESTEE LAUDER", which is a retexturizing complex for hands and chest, contains a silicone gel material including an organopolysiloxane material and octamethylcyclotetrasiloxane. As can be readily appreciated, this composition is not a deodorant or antiperspirant, and also does not include the various active cosmetic materials from which the active cosmetic materials of the present invention are selected.

Depending on the amount of organopolysiloxane material included in the cosmetic composition, the cosmetic composition can be any of various types of solid composition. For example, the composition can include an amount of organopolysiloxane sufficient to provide a cream composition as the final product. Of course, where increased amounts of the organopolysiloxane material are included in the composition, thicker (more viscous) solid cosmetic compositions can be provided.

As indicated previously, the active cosmetic material can be selected from various different cosmetic materials, including deodorant active materials, antiperspirant active materials, sunscreen materials, insect repellents and anti-fungal agents, to thereby provide, respectively, deodorant compositions, antiperspirant compositions, sunscreen compositions, insect repellent compositions and anti-fungal compositions. The active cosmetic material should be incorporated in the composition in an amount sufficient to have a functional effect. That is, where a deodorant active material is incorporated in the composition, a sufficient amount of such material should be incorporated such that, upon depositing the composition on the skin, e.g., in axillary regions of the human body, the deodorant active material acts to at least reduce (and, desirably, prevent) body malodor from axillary regions of the human body.

Some antiperspirant active materials, when utilized in amounts less than that which reduces flow of perspiration, have deodorant effects. Incorporating such lesser amounts of antiperspirant active materials, which would still achieve an object of the present invention of reducing body malodor, are still within the scope of the present invention.

Desirably, the organopolysiloxane material is a reaction product of a polysiloxane and a cross-linking agent. Illustratively, the reactants for forming the organopolysiloxane material are a vinyl-terminated siloxane polymer (e.g., a silicone rubber which is vinyl-terminated) and a hydride cross-linking agent; the reaction between this siloxane polymer and the cross-linking agent is preferably performed in the presence of a platinum catalyst.

In the composition of the present invention the volatile silicone material acts to swell the gelling agent, so as to form the silicone gel material. The volatile silicone material is, e.g., trapped in a matrix of the organopolysiloxane gelling agent in the final product, thereby forming the silicone gel material.

The cosmetic compositions according to the present invention are easy to manufacture, being formed by a mixing of the active cosmetic material and the silicone gel material. A desirable feature of the present invention is that this mixing can be performed at ambient (room) temperatures, thereby avoiding the need for high-temperature processing, including melting of components and mixing at high temperatures.

After the compositions according to the present invention have been formed, they can be introduced into dispensing containers as known in the art. For example, where a cream composition is formed, this composition can be introduced and packaged in containers which have the appearance of a stick, but which dispense product through apertures in the top surface of the package. In use, the product is extruded onto the top surface of the package through these apertures, and the product on the top surface is rubbed, e.g., on the axillary region of the human body, so as to deposit the product containing the active cosmetic material (for example, deodorant and/or antiperspirant active material) thereon.

Accordingly, through use of the present invention a cosmetic composition (such as a deodorant or antiperspirant active composition) can be provided, which leaves substantially no visible residue (for example, leaves no visible (white) residue on the skin after application and after drying of the deposited film), yet which has good cosmetic properties (including a silky and non-greasy feel upon application). Moreover, the product exhibits reduced syneresis (for example, exhibits no syneresis of the silicone material). A cream composition, which is highly efficacious and has the aforementioned excellent cosmetic properties, can be provided. In addition, compositions according to the present invention are easy to manufacture, and can be formed using room (ambient) temperature processing. The compositions according to the present invention can contain no conventional waxes, and have good efficacy and provide long-lasting fragrance substantivity (for example, the fragrance can be entrapped in the matrix of the gelling agent).

DETAILED DESCRIPTION OF THE INVENTION

While the present invention will be described in connection with specific and preferred embodiments, it will be understood that it is not intended to limit the invention to those embodiments. To the contrary, it is intended that the present invention cover all alterations, modifications and equivalents as may be included within the spirit and scope of the invention as defined by the appended claims.

Throughout the present disclosure, the present invention is described primarily in connection with an antiperspirant or deodorant composition, including antiperspirant and deodorant cream compositions. However, the present invention is not limited to such compositions; for example, the composition according to the present invention can be a sunscreen composition. Depending on the active cosmetic ingredients included in the composition, the composition can be an insect repellent composition, a sunscreen composition, an anti-fungal composition, etc. As to various types of cosmetic compositions and active materials incorporated therein, applicable to the present invention, attention is directed to U.S. Pat. No. 4,322,400 to Yuhas, the contents of which are incorporated herein by reference in their entirety.

Thus, while the present invention will primarily be described in connection with antiperspirant and deodorant compositions, for application to the skin, particularly in axillary regions of the human body, in order to reduce body malodor, e.g., by reducing the flow of perspiration in the axillary regions, the present invention is not limited to these specific uses, and, as described previously, can include various active cosmetic materials in order to achieve specific cosmetic effects for the skin.

Throughout the present specification, "deodorant active" materials and "antiperspirant active" materials are discussed. Both types of materials contribute to reduction of body (for example, axillary) malodor. By reduction of body malodor is meant that, generally, there is less body malodor after application of the composition to a person's skin, as compared to body malodor of the person without application of the composition. Such reduction can be due to a masking of the malodor, absorption and/or chemical reaction of the malodorous materials, reduction of the levels of the bacteria producing the malodorous materials, e.g., from perspiration, reduction of perspiration, etc. The antiperspirant materials, when utilized in appropriate amounts, primarily act to reduce malodor by reducing production of perspiration; the antiperspirant materials can also have a deodorant function, e.g., as an antimicrobial agent. The deodorant active materials do not substantially reduce the production of perspiration, but reduce malodor in other ways, e.g., as fragrances masking the malodor or reducing the malodor intensity, as odor adsorbents, as antimicrobial (bacteriostatic) agents, as agents chemically reacting with malodorous material, etc.

Throughout the specification, where compositions are described as including or comprising specific components or materials, or methods are described as including or comprising specific processing steps, it is contemplated by the inventors that the compositions and methods of the present invention also consist essentially of, or consist of, the recited components or materials, or the recited steps. Accordingly, throughout the present disclosure any described composition of the present invention can consist essentially of, or consist of, the recited components or materials, and any method can consist essentially of, or consist of, the recited steps.

The present invention contemplates a cosmetic composition (e.g., a solid (solidified) cosmetic composition) containing (1) an active cosmetic material selected from the group consisting of deodorant active materials, antiperspirant active materials, sunscreen materials, insect repellents and anti-fungal agents, and (2) a silicone gel material acting as a carrier for the active material and providing the composition to be a solid composition. The silicone gel material includes an organopolysiloxane material as the gelling agent and a volatile silicone material which is the base material of the gel. Illustratively, the active cosmetic material (e.g., antiperspirant active metal salt) can be in particulate form, suspended in the silicone gel material; but it need not be in such particulate form.

Desirably, the organopolysiloxane material is a silicone rubber, which can be swelled by the volatile silicone material so as to form the silicone gel material. The silicone gel material can be made, e.g., by mixing or blending the silicone rubber and volatile silicone material (for example, cyclomethicone) at a high shear rate.

Illustratively, the organopolysiloxane material is a reaction product using a polysiloxane as a reactant; more specifically, it is a reaction product of a vinyl-terminated siloxane polymer and a hydride cross-linking agent, the reaction being performed in the presence of a platinum catalyst. Preferably, the reaction takes place in the presence of the volatile silicone material, such that the volatile silicone material can easily be incorporated within a matrix of the reaction product so as to provide the silicone gel material.

The above-described reaction between the vinyl-terminated siloxane polymer and the hydride cross-linking agent is an addition curing technique for forming the organopolysiloxane. However, the present invention is not to be limited to use of organopolysiloxanes or silicone rubbers formed by such addition curing technique. That is, organopolysiloxanes (silicone rubbers) formed by condensation curing or free radical curing techniques can also be used as part of the present invention.

In the condensation cure system, a linear silanol terminated fluid can be reacted with a tri-organoxy silane or a silicate as a cross-linking agent, for example, in the presence of tin compounds as a catalyst, to form the silicone rubber, curing being based on building up the molecular weight and cross-linking. In the free radical curing system, a peroxide or radiation (illustratively, at doses of 2–5 Mrad) is used to initiate cross-linking.

An illustrative silicone gel material according to the present invention is Gransil GCM, which is a product of Grant Industries, Inc. (Elmwood Park, N.J.) containing octamethylcyclotetrasiloxane and organopolysiloxane. This material is a colorless to transparent paste having a non-volatile content of 10% by weight.

Another material which can be utilized as the silicone gel material according to the present invention is the product KSG-17 of Shin-Etsu Chemical Co., Ltd. (Tokyo, Japan). This material is described as a cyclic dimethylsilicone thickener which is a colorless, transparent paste and utilizes octamethylcyclotetrasiloxane (cyclomethicone) as the base fluid.

Another material which can be utilized as the silicone gel material, having an advantage of reduced cost, is GRANSIL SR-CYC, a product of Grant Industries, Inc. (Elmwood Park, N.J.). This product is a mixture of cyclomethicone and stearyl-vinyl/hydromethylsiloxane copolymer.

Various silicone rubbers can be used as the polyorganosiloxane of the silicone gel material of the present invention. These silicone rubbers can be combined with a volatile silicone material (e.g., cyclomethicone) to form the silicone gel material of the present invention.

As indicated previously, the organopolysiloxane material is desirably a cross-linked polydimethylsiloxane, formed as a reaction product of a vinyl-functionalized (e.g., vinyl-terminated) siloxane polymer and a hydride cross-linking agent. Various vinyl-terminated polydimethylsiloxanes are manufactured by Huls America, Inc. (Piscataway, N.J.) and include VEB-500, VEB-1,000, VEB-3,500, VEB-10,000, VEB-20,000, VEB-60,000, VEB-165,000, CPS438, CPS441, CPS441.2, CPS442, CPS443, CPS444 and CPS445. Various hydride cross-linking agents (e.g., hydride-containing silicones) are also made by Huls America, Inc. and are designated as CPS122.5, CPS123, CPS123.8 and NM203.

Various vinyl-functionalized polydimethylsiloxanes which can be used for providing the organopolysiloxane of the silicone gel material of compositions of the present invention are disclosed in the following patent documents: European Patent Application (EPA) No. 0410697 (Jan. 30, 1989); EPA No. 0431979 (Jun. 6, 1991); EPA No. 0444960 (Apr. 9, 1991); EPA No. 0501791 (Feb. 9, 1992); EPA No. 0475439 (Mar. 8, 1992); EPA No. 0614658 (Feb. 3, 1994); EPA No. 0688828 (Dec. 27, 1995); Japanese Laid-Open Application (JK) No. 62-143971 (Dec. 17, 1985); JK No. 62-143970 (Dec. 17, 1985); U.S. Pat. No. 4,698,386; U.S. Pat. No. 5,086,147; U.S. Pat. No. 5,266,321; U.S. Pat No. 5,279,890; U.S. Pat. No. 5,412,004; U.S. Pat. No. 5,466,442; and U.S. Pat. No. 5,466,849.

The reaction between the vinyl-terminated siloxane polymer and the hydride cross-linking agent is preferably performed in the presence of a platinum catalyst. Various platinum catalysts for this reaction are also available from H üls America, Inc., designated as CPC072, CPCO75 and CPC085.

The reaction product (hydrosilation product) used as the organopolysiloxane material according to the present invention includes materials used in other areas such as in the electronics area, and includes room temperature vulcanized (RTV) silicones.

The volatile silicone material utilized in providing the silicone gel material for forming the composition of the present invention can be conventional cyclic and linear volatile silicones, acting as a swelling agent for the organopolysiloxane. Illustratively, and not limiting, the volatile silicone can be a cyclomethicone, including (but not limited to) octamethylcyclotetrasiloxane (tetramer component) and decamethylcyclopentasiloxane (pentamer component). Linear volatile silicones, known in the art, could also be used as the volatile silicone material for forming the silicone gel material according to the present invention.

Desirably, where the organopolysiloxane is formed by reacting a vinyl-terminated siloxane polymer and a hydride cross-linking agent (e.g., a hydride-containing silicone), the reaction takes place in the presence of the volatile silicone material (as well as in the presence of a platinum catalyst), whereby the swelled material (silicone gel material), having the volatile silicone material trapped in a matrix of the gelling agent, is easily achieved.

The silicone gel material includes an amount of the organopolysiloxane material such that the cosmetic composition as a whole is a solid composition (e.g., a soft solid or semi-solid, such as a cream). Illustratively, and not limiting, the silicone gel material includes 2%–30% by weight, of the total weight of the silicone gel material, of the organopolysiloxane material; 98%–70% by weight, of the total weight of the silicone gel material, can be the volatile silicone material (e.g., cyclomethicone).

Thus, where the cosmetic composition contains, as the silicone gel material, a cross-linked polydimethylsiloxane and cyclomethicone, the composition can include 2%–30% by weight, of the total weight of the silicone gel material, of the cross-linked polydimethylsiloxane, and 98%–70% by weight, of the total weight of the silicone gel material, of the cyclomethicone. These amounts are merely illustrative, and are not limiting of the present invention.

The silicone gel material can be formed by blending the organopolysiloxane and volatile silicone material together, such that the volatile silicone material causes the organopolysiloxane to swell. Illustratively, and not of a limiting nature, a silicone rubber (e.g., a cross-linked polydimethylsiloxane) and cyclomethicone can be mixed in a high shear blender at ambient temperature, to form gelled cyclomethicone as the silicone gel material.

Also illustratively, the silicone gel material can be included in the cosmetic composition in an amount of 10%–80% by weight, of the total weight of the cosmetic composition.

As indicated previously, the active cosmetic material can be any of various active materials, including (but not limited to) deodorant active materials and antiperspirant active materials.

Where the composition is an antiperspirant composition, various antiperspirant active materials can be incorporated in the composition. These include, by way of example (and not of a limiting nature), aluminum chlorohydrate, aluminum chloride, aluminum sesquichlorohydrate, zirconyl hydroxychloride, aluminum-zirconium hydroxychlorides, aluminum-zirconium glycine complex (e.g., aluminum-zirconium tetrachlorohydrexgly), etc. Generally, Category I active antiperspirant ingredients listed in the Food and Drug Administration's Monograph on antiperspirant drug products for over-the-counter human use (Oct. 10, 1993) can be used. In addition, any new drug, not listed in the Monograph, such as aluminum nitratohydrate and its combination with zirconyl hydroxychlorides and nitrides, or aluminum-stannous chlorohydrates, can be incorporated as an antiperspirant active ingredient in antiperspirant compositions according to the present invention.

The antiperspirant active material, desirably, is included as a particulate suspended in the composition of the present invention, in amounts up to, e.g., 30% by weight, of the total weight of the composition. This is an illustrative amount, and is not limiting of the present invention. As an illustrative minimum amount, and not to be limiting, the composition could include at least 0.1% by weight antiperspirant active material, of the total weight of the composition; however, at low amounts the material may not reduce perspiration (for example, may act as a deodorant active material, such as an antimicrobial agent, rather than to reduce perspiration).

Where the composition is a deodorant composition or a deodorant/antiperspirant composition, appropriate deodorant active materials can be incorporated in the composition, so as to provide deodorant active materials for combatting body malodor. For example, a deodorant fragrance and/or antimicrobial agent (bacteriostat) can be incorporated. A fragrance would, illustratively, be incorporated in an amount of 0.5%–3.0% by weight, of the total weight of the composition; the antimicrobial/bacteriostat material, such as Triclosan, would preferably and illustratively be included in an amount of from 0.1% to 0.5% by weight, of the total weight of the composition.

Illustratively, compositions according to the present invention are substantially anhydrous. Moreover, they are free of conventional gelling agents such as fatty alcohols (e.g., stearyl alcohol) and hydrogenated castor oil.

The compositions according to the present invention can include other ingredients conventionally incorporated in cosmetic compositions, including (but not limited to) perfumes, cosmetic powders, colorants and emulsifiers. As for various other ingredients which can be incorporated, attention is directed to the optional components such as the colorants, perfumes and fillers described in the following U.S. Patents:

U.S. Pat. No. 5,019,375 to Tanner, et al. (the contents of which are incorporated herein by reference in their entirety);

U.S. Pat. No. 4,937,069 to Shin (the contents of which are incorporated herein by reference in their entirety); and U.S. Pat. No. 5,102,656 to Kasat (the contents of which have previously been incorporated herein by reference in their entirety).

Compositions according to the present invention can be made by mixing the active cosmetic material and the silicone gel material; this mixing can be done, desirably, at room (ambient) temperature, so as to avoid expenses in heating and cooling the composition components, and loss of materials due, e.g., to volatilization at elevated temperatures. Illustratively (and not to limit the present invention), compositions according to the present invention can be made by mixing at a temperature in the range of 20°–35° C., preferably 23°–28° C. The mixture can be introduced into dispensing canisters, as with conventional solid compositions (e.g., conventional cream compositions). Where the solid composition is a cream (soft solid), these dispensing canisters can be canisters which have a top surface with slots therein, the composition being dispensed onto the top surface from a reservoir in the canister, and then rubbed on the skin from the top surface so as to deposit a film of the product on the skin.

Illustratively, where the composition is an antiperspirant composition containing an antiperspirant active material for reducing perspiration in axillary regions, the composition is extruded from inside the dispensing canister through the slots onto the top surface of the dispensing canister, and from there is applied (rubbed) on the skin in the axillary regions, so as to deposit sufficient antiperspirant active material (and, if present, sufficient deodorant active material) so as to reduce perspiration and reduce body malodor originating in axillary regions of the human body.

In the following, specific examples of compositions within the scope of the present invention are set forth. Of course, these specific examples are illustrative of the present invention, and are not limiting. In these examples, the amounts of the components are in weight percent, of the total weight of the composition. In these examples, as well as throughout the present specification, various names utilized are the CTFA (Cosmetics, Toiletry and Fragrance Association, Inc.) names, as set forth in the *CTFA International Cosmetic Ingredient Dictionary* (4th Ed. 1991).

EXAMPLE 1

| Ingredient | Amount |
| --- | --- |
| Gransil SR-CYC | 26.40 |
| Cyclomethicone | 53.60 |
| Aluminum-Zirconium Tetrachlorohydrex GLY | 20.00 |
| | 100.00 |

EXAMPLE 2

| Ingredients | Amount |
| --- | --- |
| Gransil GCM (Gelled Cyclomethicone) | 75.0 |
| Aluminum-Zirconium Tetrachlorohydrex GLY | 25.0 |
| | 100.0 |

EXAMPLE 3

| Ingredients | Amount |
| --- | --- |
| Gransil GCM | 75.0 |
| Aluminum-Zirconium Tetrachlorohydrex GLY (Reach AZP 908-0) (Reheis) | 25.0 |
| | 100.0 |

EXAMPLE 4

| Ingredient | Amount |
| --- | --- |
| Gransil GCM | 70.0 |
| Aluminum-Zirconium Tetrachlorohydrex GLY | 20.0 |
| Dimethicone 50CS | 10.0 |
| | 100.0 |

EXAMPLE 5

| Ingredient | Amount |
| --- | --- |
| Gransil GCM | 67.5 |
| Aluminum-Zirconium Tetrachlorohydrex GLY | 22.0 |
| Dimethicone | 10.0 |
| Fumed Silica (Cabosil M5, from Cabot Corp.) | 0.5 |
| | 100.0 |

EXAMPLE 6

| Ingredient | Amount |
| --- | --- |
| Gransil GCM | 72.5 |
| Aluminum-Zirconium Tetrachlorohydrex GLY | 22.0 |
| Dimethicone | 2.5 |
| Fumed Silica (Cabosil M5, from Cabot Corp.) | 0.5 |
| Phenyltrimethicone | 2.5 |
| | 100.0 |

EXAMPLE 7

| Ingredient | Amount |
| --- | --- |
| Gransil GCM | 70.0 |
| Aluminum-Zirconium Tetrachlorohydrex GLY | 22.0 |
| Dimethicone | 5.0 |
| Fumed Silica (Cabosil M5, from Cabot Corp.) | 0.5 |
| Phenyltrimethicone | 2.5 |
| | 100.0 |

EXAMPLE 8

| Ingredient | Amount |
| --- | --- |
| Gelled Cyclomethicone | 99.50 |
| Triclosan | 0.50 |
| | 100 |

EXAMPLE 9

| Ingredient | Amount |
| --- | --- |
| Gelled Cyclomethicone | 99.75 |
| Triclosan | 0.25 |
| | 100 |

EXAMPLE 10

| Ingredient | Amount |
| --- | --- |
| Gelled Cyclomethicone | 99.75 |
| Triclosan | 0.01 |
| | 100 |

EXAMPLE 11

| Ingredient | Amount |
| --- | --- |
| Gransil GCM | 99.0 |
| Fragrance | 1.0 |
| | 100% |

In the foregoing Examples 2–7, the compositions were formed by mixing the materials with a rotary mixer at ambient temperature, to a viscous opaque gel. In Examples 8–10 the gelled cyclomethicone and Triclosan components were mixed with a stirrer at ambient temperature, to form a thick uniform gel. In Example 11, the product had good slip characteristics, and the fragrance was compatible with the silicone gel material, the composition being clear after fragrance incorporation. The foregoing Examples 1–7 formed antiperspirant compositions, while Examples 8–11 are deodorant compositions.

Thus, according to the present invention, a cosmetic composition (e.g, a solid cosmetic composition, such as a cream composition) containing an active cosmetic material (including, but not limited to, deodorant and antiperspirant active materials) can be provided which is efficacious and exhibits no visible residue (upon application or after drying). This composition has good cosmetic properties, including a silky and non-greasy feel, and exhibits reduced syneresis of silicone. Moreover, this composition is easy to manufacture, and can be produced utilizing processing at room (ambient) temperatures. Moreover, this composition need not contain wax gellants or clay or particulate thickening agents, and is anhydrous.

While we have shown and described several embodiments in accordance with the present invention, it is understood that the same is not limited thereto, but is susceptible to numerous changes and modifications as known to one having ordinary skill in the art, and we therefore do not wish to be limited to the details shown and described herein, but intend to cover all such modifications as are encompassed by the scope of the appended claims.

What is claimed is:

1. A cosmetic composition, comprising:
    (a) an active cosmetic material selected from the group consisting of deodorant active materials and antiperspirant active materials in an amount sufficient to have a functional effect; and
    (b) a silicone gel material, having the active cosmetic material incorporated therein, the silicone gel material including a volatile silicone material and a cross-linked organopolysiloxane material which is a reaction product of a polysiloxane and a cross-linking agent, the organopolysiloxane material being included in the cosmetic composition in an amount sufficient to provide a solid cosmetic composition, the volatile silicone material being included in the cosmetic composition in an amount such that the organopolysiloxane material can form a gel therefrom at room temperature.

2. The cosmetic composition according to claim 1, wherein the organopolysiloxane material is a reaction product using a polysiloxane as a reactant.

3. The cosmetic composition according to claim 1, wherein the organopolysiloxane material is a reaction product of a vinyl-terminated siloxane polymer and a hydride cross-linking agent, a reaction forming the reaction product taking place in the presence of the volatile silicone material.

4. The cosmetic composition according to claim 3, wherein the reaction is performed in the presence of a platinum catalyst.

5. The cosmetic composition according to claim 3, wherein the volatile silicone material is incorporated within a matrix of the reaction product.

6. The cosmetic composition according to claim 2, wherein the reaction product is a cross-linked polydimethylsiloxane.

7. The cosmetic composition according to claim 6, wherein the volatile silicone material is cyclomethicone.

8. The cosmetic composition according to claim 7, wherein the cross-linked polydimethylsiloxane is included in the composition in an amount of 2%–30% by weight, of the total weight of the silicone gel material.

9. The cosmetic composition according to claim 8, wherein the cyclomethicone is included in the composition in an amount of 98%-70% by weight, of the total weight of the silicone gel material.

10. The cosmetic composition according to claim 9, wherein the silicone gel material is included in the composition in an amount of 10%–80% by weight, of the total weight of the composition.

11. The cosmetic composition according to claim 10, wherein the active cosmetic material is selected from the group consisting of deodorant active materials and antiperspirant active materials.

12. The cosmetic composition according to claim 11, wherein the active cosmetic material includes antiperspirant active materials.

13. The cosmetic composition according to claim 12, wherein the composition includes a sufficient amount of the cross-linked polydimethylsiloxane so as to form a cream composition.

14. The cosmetic composition according to claim 11, wherein the active cosmetic material includes deodorant active materials.

15. The cosmetic composition according to claim 14, wherein the composition includes a sufficient amount of the cross-linked polydimethylsiloxane so as to form a cream composition.

16. The cosmetic composition according to claim 1, wherein the composition includes a sufficient amount of the organopolysiloxane material so as to form a cream composition.

17. The cosmetic composition according to claim 1, wherein the organopolysiloxane material is included in the composition in an amount of 2%–30% by weight, of the total weight of the silicone gel material.

18. The cosmetic composition according to claim 17, wherein the silicone gel material is included in the composition in an amount of 10%–80% by weight, of the total weight of the composition.

19. The cosmetic composition according to claim 1, wherein the silicone gel material is a gelled cyclomethicone.

20. The cosmetic composition according to claim 1, wherein the active cosmetic material is selected from the group consisting of antiperspirant active materials and deodorant active materials, whereby the cosmetic composition is an antiperspirant or deodorant composition.

21. The cosmetic composition according to claim 20, wherein the active cosmetic material is an antiperspirant active material, said antiperspirant active material being incorporated in the composition in an amount sufficient to reduce flow of perspiration from axillary regions of a human body.

22. The cosmetic composition according to claim 21, wherein the antiperspirant active material includes an antiperspirant aluminum salt.

23. The cosmetic composition according to claim 20, wherein the active cosmetic material includes a deodorant active material, the deodorant active material including a bacteriostat.

24. The cosmetic composition according to claim 20, wherein the composition includes a fragrancing material.

25. The cosmetic composition according to claim 1, wherein the organopolysiloxane material is a silicone rubber.

26. The cosmetic composition according to claim 25, wherein the volatile silicone material is cyclomethicone.

27. Solid antiperspiration composition, for application to a human, comprising:
  (a) an active antiperspirant material, in an amount sufficient to have an antiperspirant effect; and
  (b) a silicone gel material, the silicone gel material having the active antiperspirant material incorporated therein, the silicone gel material including an organopolysiloxane material and a volatile silicone material, the silicone gel material containing, in % by weight of the total weight of the silicone gel material, 2%–30% of the organopolysiloxane and 98%-70% of the volatile silicone material, the composition containing, in % by weight of the total weight of the composition, 10%–80% of the silicone gel material.

28. Solid antiperspirant composition according to claim 27, wherein the organopolysiloxane is a cross-linked polydimethylsiloxane.

29. Solid antiperspirant composition according to claim 28, wherein the cross-linked polydimethylsiloxane is a reaction product of a vinyl-terminated polydimethylsiloxane cross-linked by a hydride cross-linking agent.

30. Solid antiperspirant composition according to claim 29, wherein the volatile silicone material is cyclomethicone.

31. Solid antiperspirant composition according to claim 30, wherein the composition is a cream composition.

32. Solid deodorant composition, for application to a human, comprising:
  (a) an active deodorant material, in an amount sufficient to have a deodorant effect; and
  (b) a silicone gel material, the silicone gel material having said active deodorant material incorporated therein, the silicone gel material including an organopolysiloxane material and a volatile silicone material, the silicone gel material including, in % by weight of the total weight of the silicone gel material, 2%–30% of the organopolysiloxane and 98%-70% of the volatile silicone material, the composition containing, in % by weight of the total weight of the composition, 10%–80% of the silicone gel material.

33. Solid deodorant composition according to claim 32, wherein said active deodorant material is a bacteriostat.

34. A method of reducing body malodor, comprising the step of applying the solid deodorant composition of claim 32 to axillary regions of the human.

35. A method of reducing body malodor, comprising the step of applying the solid antiperspirant composition of claim 31 to axillary regions of the human.

36. A method of reducing body malodor, comprising the step of applying the solid antiperspirant composition of claim 27 to axillary regions of the human.

37. A method of reducing body malodor of a human, comprising the step of applying the cosmetic composition of claim 20 to axillary regions of the human.

38. A method of forming a cosmetic composition, comprising the step of mixing an active cosmetic material with a silicone gel material, the active cosmetic material being selected from the group consisting of deodorant active materials, antiperspirant active materials, sunscreen materials, insect repellents, and anti-fungal agents, the active cosmetic material being included in an amount sufficient to have a functional effect; and the silicone gel material including an organopolysiloxane material and a volatile silicone material, the organopolysiloxane material being included in the composition in an amount sufficient to form a solid cosmetic composition, the volatile silicone material being included in the composition in an amount sufficient such that the organopolysiloxane material can form a gel therefrom.

39. The method according to claim 38, wherein the mixing is performed at ambient temperature.

40. The method according to claim 38, further including the step of forming the silicone gel material, the step of forming the silicone gel material including reacting a vinyl-terminated siloxane polymer with a hydride cross-linking agent to form the organopolysiloxane material.

41. The method according to claim 40, wherein said reacting is performed in the presence of a platinum catalyst.

42. The method according to claim 41, wherein said reacting is performed in the presence of said volatile silicone material.

43. The method according to claim 42, wherein said volatile silicone material is cyclomethicone.

44. The method according to claim 40, wherein said reacting is performed in the presence of said volatile silicone material.

45. The method according to claim 38, further including forming the silicone gel material by mixing a silicone rubber and cyclomethicone.

46. The method according to claim 38, wherein the composition includes a sufficient amount of the organopolysiloxane material so as to form a cream composition.

* * * * *